US011553904B2

(12) United States Patent
Suzuki et al.

(10) Patent No.: US 11,553,904 B2
(45) Date of Patent: Jan. 17, 2023

(54) CELL ISOLATION INSTRUMENT

(71) Applicant: NIHON KOHDEN CORPORATION, Tokorozawa (JP)

(72) Inventors: Akane Suzuki, Tokyo (JP); Takahiro Shioyama, Tokyo (JP)

(73) Assignee: NIHON KOHDEN CORPORATION, Tokorozawa (JP)

( * ) Notice: Subject to any disclaimer, the term of this patent is extended or adjusted under 35 U.S.C. 154(b) by 216 days.

(21) Appl. No.: 15/403,941

(22) Filed: Jan. 11, 2017

(65) Prior Publication Data

US 2017/0196544 A1 Jul. 13, 2017

(30) Foreign Application Priority Data

Jan. 12, 2016 (JP) .............................. JP2016-003181

(51) Int. Cl.
| | |
|---|---|
| *A61B 10/06* | (2006.01) |
| *B01L 3/00* | (2006.01) |
| *A61B 10/00* | (2006.01) |
| *A61B 17/30* | (2006.01) |

(52) U.S. Cl.
CPC .......... *A61B 10/06* (2013.01); *A61B 10/0096* (2013.01); *A61B 17/30* (2013.01); *B01L 3/502* (2013.01); *B01L 3/5082* (2013.01); *B01L 3/50825* (2013.01); *B01L 2300/041* (2013.01); *B01L 2300/046* (2013.01);
(Continued)

(58) Field of Classification Search
CPC ..... A61B 10/06; A61B 10/0096; A61B 17/30; A61B 5/150351; B01L 3/5082; B01L 3/502; B01L 2300/0858; B01L 2300/123; B01L 2300/0832; B01L 2300/0681; B01L 3/50825; B01L 2300/041; B01L 2300/046
USPC ......................................................... 600/562
See application file for complete search history.

(56) References Cited

U.S. PATENT DOCUMENTS

| | | | | |
|---|---|---|---|---|
| 3,080,760 | A * | 3/1963 | Piersma ................... | G01N 1/12 73/863.31 |
| 3,437,206 | A * | 4/1969 | Kusik ................... | A61M 5/165 210/251 |

(Continued)

FOREIGN PATENT DOCUMENTS

| | | |
|---|---|---|
| JP | H01136460 U | 9/1989 |
| JP | 2009036732 A | 2/2009 |

(Continued)

OTHER PUBLICATIONS

"Young's Modulus—Tensile and Yield Strength for Common Materials." Young's Modulus of Elasticity for Metals and Alloys, www.engineeringtoolbox.com/young-modulus-d_417.html.*
(Continued)

*Primary Examiner* — Alex M Valvis
*Assistant Examiner* — Chanel J Jhin
(74) *Attorney, Agent, or Firm* — Dorsey & Whitney LLP (57) ABSTRACT

Provided is a cell isolation instrument capable of smoothly performing a plurality of steps associated with isolation of cells, including gripping of a biological tissue, transferring of the biological tissue, and isolating of the biological tissue. A container has an opening. A sealing member seals the opening. A pair of pinching parts is connected to the sealing member, and the pair of pinching parts opens or closes by being pressed.

20 Claims, 7 Drawing Sheets

(52) U.S. Cl.
CPC .............. *B01L 2300/0681* (2013.01); *B01L 2300/0832* (2013.01); *B01L 2300/0858* (2013.01); *B01L 2300/123* (2013.01)

(56) References Cited

U.S. PATENT DOCUMENTS

| | | | | |
|---|---|---|---|---|
| 3,705,018 | A * | 12/1972 | Taylor | B01L 3/5082 422/501 |
| 4,690,153 | A * | 9/1987 | Losada | A61B 5/150022 600/576 |
| 4,967,763 | A * | 11/1990 | Nugent | B01L 3/5082 422/914 |
| 5,269,804 | A * | 12/1993 | Bales | A61B 17/320016 606/205 |
| 2005/0125013 | A1 * | 6/2005 | Kessler | A61B 17/062 606/148 |
| 2008/0255427 | A1 * | 10/2008 | Satake | A61B 17/10 600/204 |
| 2011/0020860 | A1 | 1/2011 | Greenwald | |
| 2011/0146420 | A1 | 6/2011 | Okada et al. | |
| 2013/0330248 | A1 * | 12/2013 | Shioyama | C12M 47/08 422/516 |
| 2013/0345596 | A1 | 12/2013 | Zimmon | |
| 2016/0008807 | A1 * | 1/2016 | Lotosky-Compton | B01L 3/5082 422/558 |

FOREIGN PATENT DOCUMENTS

| | | |
|---|---|---|
| JP | 2014041018 A | 3/2014 |
| WO | 2010024042 A1 | 3/2010 |

OTHER PUBLICATIONS

First Office Action dated Jan. 18, 2019 for European application No. 16207519.6.
English translation of Notification of Reasons for Refusal received in JP Application No. 2016-003181 dated Sep. 27, 2019.
Office Action for EP Application No. 16207519.6, dated Nov. 28, 2019.

* cited by examiner

CELL ISOLATION INSTRUMENT

CROSS-REFERENCE TO RELATED APPLICATIONS(s)

This application claims priority to Japanese Application No. JP 2016-003181 filed Jan. 12, 2016, which is incorporated herein by reference, in its entirety, for any purpose.

BACKGROUND

The present invention relates to a cell isolation instrument, and particularly relates to a cell isolation instrument, with which cells are isolated from a biological tissue.

In a medical institution, a cytotechnologist or a pathologist makes a diagnosis using a section of tissues collected from a test subject. However, a specimen from a frozen section often results in an incomplete specimen. Further, it is difficult to determine some cases by the above-mentioned diagnosis in which only one cross section of a tissue can be observed. Therefore, a method in which cells are isolated from a biological tissue collected from a test subject and the cells are analyzed by a flow cytometer has been used.

In a step of isolating cells from a biological tissue, a plurality of steps is required, and also a skilled technique is needed. Due to this, a technique for accurately and rapidly isolating cells has been demanded. In particular, a biological tissue associated with a digestive organ is fibrous, and therefore, it is necessary to accurately isolate cells from the biological tissue.

JP-A-2014-41018 (Patent Document 1) discloses a homogenizing device for isolating cells from a biological tissue. The homogenizing device is configured to rotate a homogenizing member while pressing the homogenizing member against a biological tissue placed in a container, thereby isolating cells from the biological tissue.

In the technique disclosed in the above Patent Document 1, a treatment in which a biological tissue is placed in a container is performed, and thereafter a pressure is applied to the biological tissue, thereby isolating cells. In this manner, an isolation treatment is performed after a biological tissue is placed in a container, and therefore, the technique has a problem that a plurality of steps (gripping of a biological tissue, transfer, and isolation cannot be smoothly performed continuously.

SUMMARY OF THE INVENTION

The invention has been made in view of the above problems, and a main object of the invention is to provide a cell isolation instrument capable of smoothly performing a plurality of steps (gripping of a biological tissue, transfer, and isolation) associated with isolation of cells.

One aspect of a cell isolation instrument according to the invention includes:
a container including an opening;
a sealing member that seals the opening, and
a pair of pinching parts which is connected to the sealing member, and the pair of pinching parts configured to open or close by being pressed.

The pinching parts which pinch a biological tissue are provided in the sealing member. The sealing member is a member which seals the container including an opening. Therefore, a medical worker can pinch (pick up) a biological tissue, and directly place the biological tissue in the container, and seal the opening. In addition, the medical worker can isolate cells from the biological tissue by pressing when the biological tissue is pinched. That is, the biological tissue can be placed in the container while performing an isolation treatment, and therefore, gripping of a biological tissue, transfer, and isolation can be smoothly performed in a series of flow.

According to the invention, a plurality of steps (gripping of a biological tissue, transfer, and isolation) associated with isolation of cells can be smoothly performed.

DETAILED DESCRIPTION

Hereinafter, embodiments of the invention will be described with reference to the drawings. In the respective drawings, the reduction scale or the like is changed as appropriate so that each member has a recognizable size.

Figure 1:
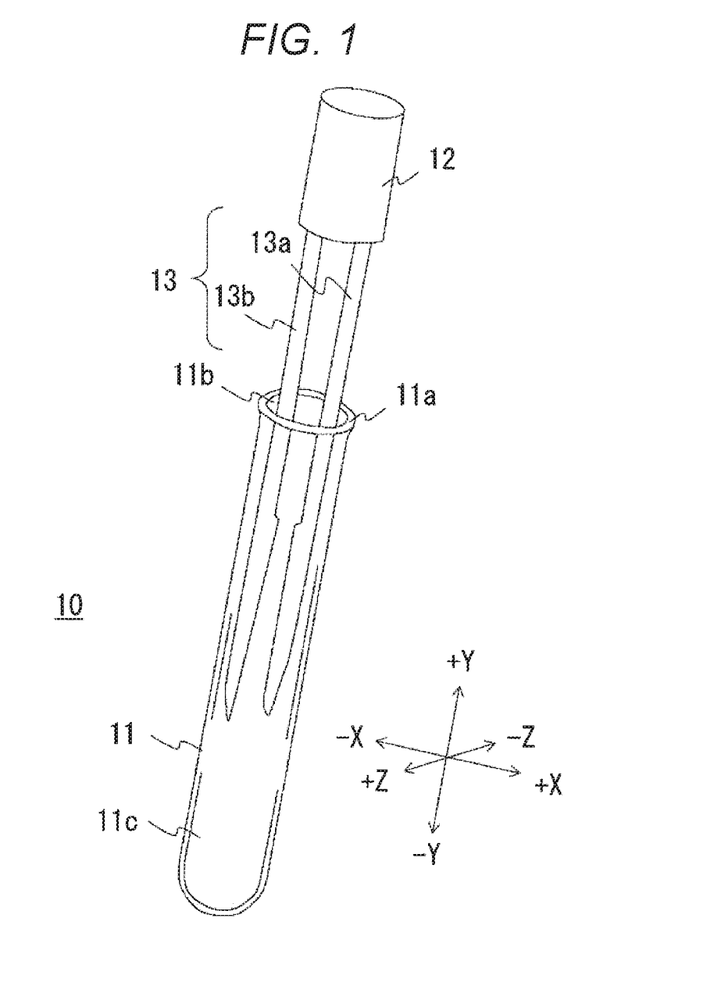
FIG. 1 is a perspective view showing the configuration of a cell isolation instrument 10 according to an embodiment of the present disclosure.

First, the configuration of a cell isolation instrument 10 according to this embodiment will be described. FIG. 1 shows the cell isolation instrument 10. The cell isolation instrument 10 includes a container 11, a sealing member 12, and pinching parts 13.

The container 11 is a cylindrical member in which an upper end surface 11a has an opening 11b and a lower end portion is a round bottom. The container 11 is desirably transparent and is desirably capable of visually recognizing a hollow inner space 11c. The inner space 11c connects to the opening 11b. The container 11 may be, for example, a glass test tube or the like, but is more preferably implemented using a material which is soft such that it is deformed by being pressed. For example, the container 11 is preferably implemented using a synthetic resin such as polypropylene or polyethylene. In other words, the container 11 desirably has an elasticity of about 0.1 to 3 GPa.

The sealing member 12 is a member which seals the opening 11b of the container 11. The outer diameter of the sealing member 12 is substantially equal to the diameter of the opening 11b of the container 11. By inserting the sealing member 12 into the opening 11b, the sealing member 12 is fixed to the container 11. To an insertion surface of the sealing member 12 into the opening 11b, the pinching parts 13 are connected.

The sealing member 12 may have any shape as long as it can seal the container 11. For example, a groove with a corresponding shape is provided in each of the inner peripheral surface of the container 11 and the outer peripheral surface of the sealing member 12, and sealing may be performed by rotating the sealing member 12 in a state where the groove of the sealing member 12 is fitted to the groove of the container 11. Alternatively, the sealing member 12 is implemented using an elastic member (for example, rubber), and sealing may be performed by inserting the sealing member 12 into the opening 11b of the container 11. The "sealing" in this embodiment is not necessarily used in a way that the container 11 is closed and brought into a hermetically sealed state, but may be used in a way that the sealing member 12 and the pinching parts 13 can be placed (or fixed) in the container 11.

The pinching parts 13 are connected to a lower end portion (an insertion surface into the opening 11b) of the sealing member 12. The pinching parts 13 are a pair of members (13a and 13b), and pinch a biological tissue and apply a pressure thereto as will be described later. The pinching parts 13 are in a state where the tips (an opposite direction to a connecting surface to the sealing member 12) are open when they are not pressed (when a force is not applied), and in the case where the pinching parts 13 are pressed from both sides in a short-side direction (which will be described later with reference to FIG. 3E), the tips are closed. The pinching parts 13 pinch a biological tissue and also act so as to crush the biological tissue. The pressing of a biological tissue by the pinching parts 13 (in other words, isolation of cells from a biological tissue) will be described later with reference to FIGS. 3A to 3E.

Incidentally, the pinching surface of the pinching part 13 desirably has a larger area than the connecting portion (in other words, a connecting portion to the sealing member 12) of the pinching part 13. According to this, a biological tissue can be reliably pinched. The pinching surface refers to a place where a biological tissue is pinched.

In the following description, the direction toward the lower end of the container 11 is defined as "−Y direction", the direction toward the upper end thereof (the direction toward the opening) is defined as "+Y direction", the opening and closing direction of the pinching parts 13 is defined as "X direction (+X direction and −X direction)", and a direction orthogonal to the opening and closing direction of the pinching part 13 is defined as "Z direction (+Z direction and −Z direction)".

FIGS. 2A to 2D are enlarged views showing examples of the configuration of the tip portions of the pinching parts 13 (13a and 13b). In an example of FIG. 2A, the pinching surfaces 131a and 131b of the pinching parts 13 have a substantially planar shape. In an example of FIG. 2B, the pinching surfaces 131c and 131d of the pinching parts 13 have a shape provided with ridges and grooves. In an example of FIG. 2C, the pinching surface 131e of the pinching part 13 has a corrugated shape like a so-called spiky frog (provided with a plurality of columnar bodies with a fine sharp tip). In an example of FIG. 2I), both of the pinching surfaces 131g and 131h of the pinching parts 13 have a corrugated shape like a so-called spiky frog (provided with a plurality of columnar bodies with a fine sharp tip). The pinching parts 13 may have any of the configurations of FIGS. 2A to 2D, however, in the configurations of FIGS. 2B to 2D, ridges and grooves are provided on the pinching surfaces (131c, 131d, 131e, 131g, and 131h) which pinch a biological tissue. Due to this, in the configurations of FIGS. 2B to 2D, even if the force to be applied is low, the biological tissue can be pressed strongly. Incidentally, in FIGS. 2B to 2D, it is more preferred that ridges and grooves are provided on the entire pinching surface, however, ridges and grooves may be provided on only a portion of the pinching surface.

Figure 2A:
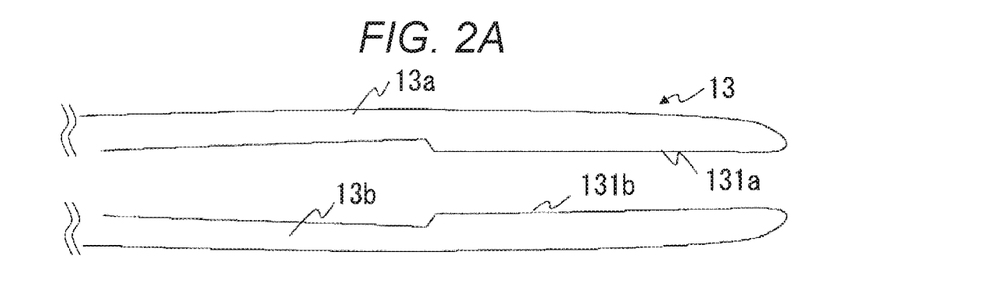
FIGS. 2A to 2D are views each showing the structure of tips of pinching parts 13 according to the embodiment of the present disclosure.
Figure 2B:
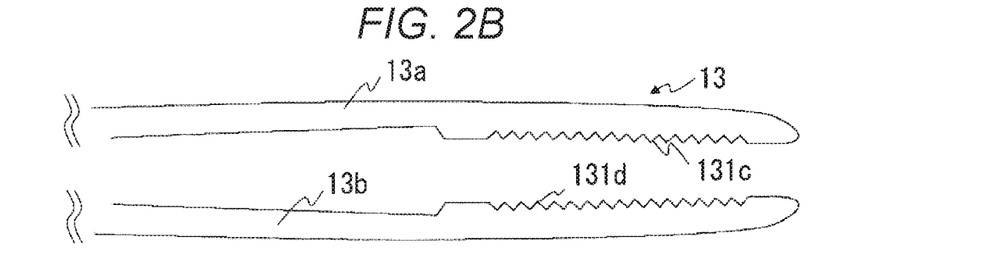
Figure 3A:
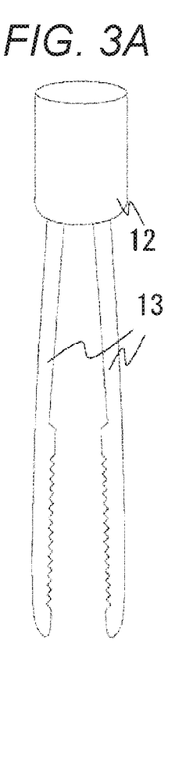
FIGS. 3A to 3E are schematic views showing the usage of the cell isolation instrument 10 according to the embodiment of the present disclosure.

Then, the usage of the cell isolation instrument 10 will be described with reference to FIGS. 3A to 3E. FIG. 3A is a view showing a state before a biological tissue t is pinched, Incidentally, in the following description, a description will be given by assuming that the same shape of the pinching surface as shown in FIG. 2B described above is adopted. In a stage before using the cell isolation instrument 10, a medical worker detaches the sealing member 12 and the pinching parts 13 from the container 11 beforehand. As described above, the pair of pinching parts 13 (13a and 13b) is in a state where the tips are separated from each other when a force is not applied thereto.

Figure 3B:
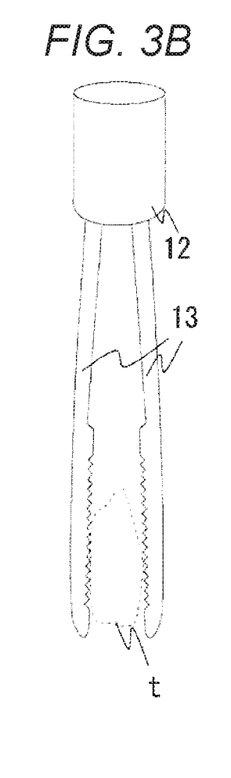

Subsequently, a state where the biological tissue t is pinched is shown in FIG. 3B. The medical worker collects a biological tissue t with a size enabling the medical worker to pinch the tissue from a test subject (including not only a human being, but also an animal) in advance. The medical worker pinches the biological tissue t with the tips of the pinching parts 13 and presses the vicinity of the middle of the pinching parts 13 (in the middle of the connection point between the tips of the pinching parts 13 and the sealing member 12) from both sides. In other words, the medical worker pinches the biological tissue t with the tips of the pinching parts 13 and then applies a pressure in the direction where the distance between the pinching part 13a and the pinching part 13b is decreased. That is, the pinching part 13a and the pinching part 13b are configured to be operable or closable (preferably, capable of coming into or out of contact with each other) depending on whether it is pressed or not.

Figure 3C:
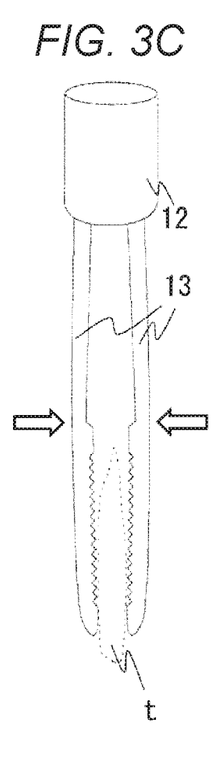

FIG. 3C is a conceptual view showing a state after the biological tissue t is pinched with the pinching parts 13 and pressed. The medical worker applies a force (applies a force in the direction indicated by the arrows) so that the biological tissue t is crushed through the pinching parts 13 as described above. By doing this, the biological tissue t is in a crushed state as compared with before it is pinched. The biological tissue t becomes soft by being crushed, and its surface area is increased. By increasing the surface area, cells are easily released from the biological tissue t. By crushing the biological tissue t in this manner, cells are in a state of being isolated (or in a state of being easily isolated) from the biological tissue t.

Figure 3D:
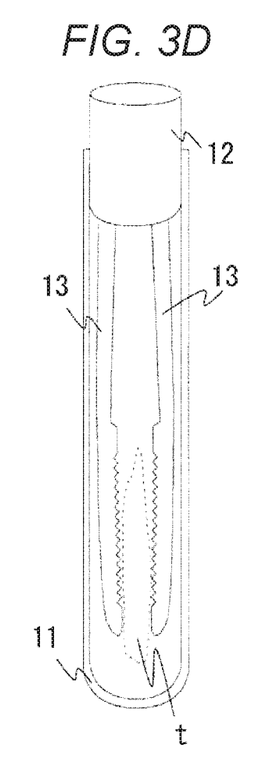

The medical worker inserts the pinching parts 13 into the container 11 in a state where the biological tissue t is pinched while crushing. This state is shown in FIG. 3D, The medical worker inserts the biological tissue t and the pinching parts 13 into the container 11 and fits the sealing member 12 to the opening 11b (not shown in FIG. 3D) of the container 11. By doing this, the biological tissue t crushed by pinching is in a state of being disposed in the container 11.

Incidentally, although not shown in the drawing, the medical worker injects a reagent (not shown) and a cell treatment solution (not shown) into the container 11 in advance before the biological tissue t is inserted into the container 11. The reagent may be any as long as it contains, for example, a surfactant, an RNA (ribonucleic acid) remover, and a fluorescent dye or pigment. The cell treatment solution is desirably a solution having substantially the same osmotic pressure as the living body such as, for example, PBS (phosphate-buffered saline).

The surfactant is used for nuclear isolation of the cells isolated from the biological tissue. The RNA remover removes RNA in the solution (the solution containing the isolated cells). Further, the fluorescent dye or pigment stains the cells subjected to nuclear isolation. By doing this, nuclear isolation of cells, removal of RNA, and staining of cells can be performed simultaneously with isolation of cells.

Figure 3E:
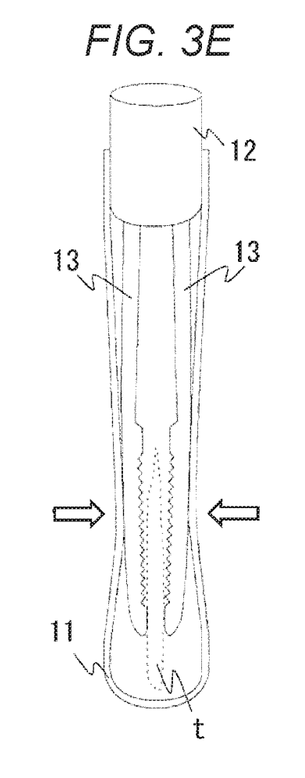

The medical worker further applies a pressure to the biological tissue t after disposing the biological tissue tin the container 11, thereby isolating cells. FIG. 3E is a view showing a method for isolating cells from the biological tissue t in the container 11.

As described above, the container 11 is soft such that it is deformed by being pressed by the medical worker (which is soft such that it can be deformed by being pressed). The Young's modulus of the container 11 may be, for example, about 0.1 GPa to 3 GPa. The medical worker applies a pressure so as to crush the container 11. By doing this, the container 11 is deformed, and a pressure is applied to the biological tissue t. Here, the Youngs modulus of the container 11 is preferably smaller than the Young's modulus of the pinching parts 13. According to this relationship of the Young's modulus (the Young's modulus of the container 11 is smaller than the Young's modulus of the pinching parts 13), the pinching parts 13 can apply a pressure to the biological tissue t while firmly pinching the biological tissue t. The medical worker repeatedly performs pressing and release of pressing for the biological tissue t through the container 11 (in other words, by alternately bringing the biological tissue t into the states of FIG. 3D and FIG. 3E a plurality of times), thereby, cells are isolated from the biological tissue t.

Incidentally, the medical worker may perform isolation of cells from the biological tissue t by repeatedly performing pressing and release of pressing in a stage before placing the biological tissue t in the container 11 (that is, in a stage of FIG. 3C). In the case where the container 11 is implemented using a hard material which is not deformed by being pressed, pressing beforehand becomes a necessary operation.

In the case where the medical worker determines that cells could be sufficiently isolated from the biological tissue t, the solution (the solution containing the isolated cells) is extracted from the container 11, and the cells are analyzed by a flow cytometer.

Next, an effect of the cell isolation instrument 10 according to this embodiment will be described. As described above, the pinching parts 13 which pinch a biological tissue are provided in the sealing member 12. The sealing member 12 seals the opening 11b. Therefore, a medical worker can pinch (pick up) a biological tissue, and directly place the biological tissue in the container 11. Further, the medical worker can increase the surface area of the biological tissue by pressing when the biological tissue is pinched, and can isolate cells from the biological tissue. That is, the biological tissue can be disposed in the container 11 while pressing, and therefore, gripping of the biological tissue, transfer, and isolation can be smoothly performed in a series of flow.

Figure 2C:
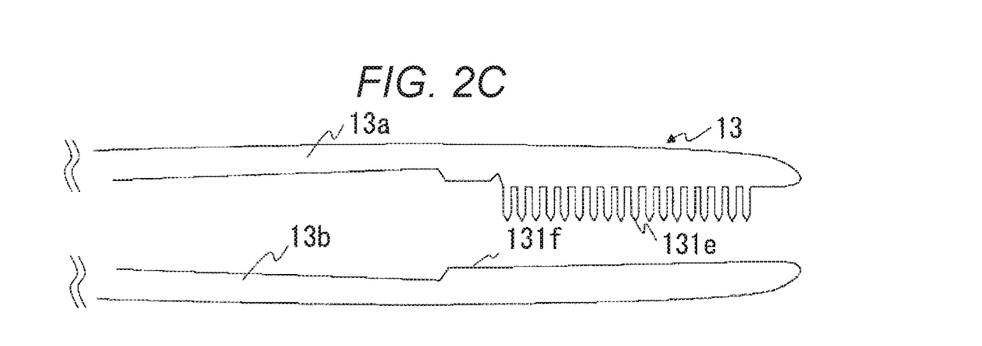
Figure 2D:
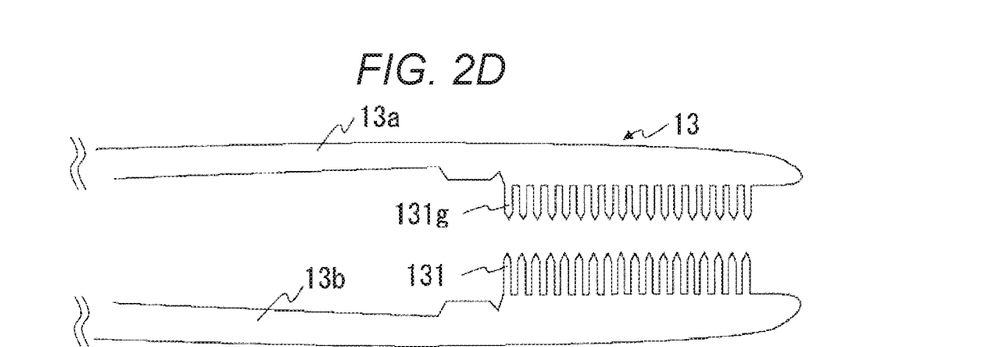

Further, the pinching parts 13 can be configured such that the pinching surface has a corrugated shape (FIGS. 2B to 2D). Since the pinching surface has ridges and grooves, the pinching parts 13 can increase the area where a pressure applied by the medical worker is applied to the biological tissue. According to this, the pressure applied by the medical worker can be efficiently transferred to the biological tissue, and thus, cells can be efficiently isolated from the biological tissue. Further, since the pinching surface has ridges and grooves, the pinching surface also functions as a slip-proof member, and can reduce the possibility that the biological tissue is dropped during transfer.

Further, it is preferred that the pinching parts 13 are in a state where the tips are open when they are not pressed by the medical worker (FIG. 1). According to this, the medical worker can handle the biological tissue by the same operation as the operation of picking up the biological tissue with fingers.

Further, it is preferred that the container 11 is soft such that it is deformed by being pressed by the medical worker. For example, the Young's modulus of the container 11 is preferably from about 0.1 to 3 GPa. According to this, the medical worker can crush the biological tissue from the outside of the container 11 (in other words, by deforming the container 11, a pressure can be applied to the biological tissue in the container 11).

Here, the Young's modulus of the pinching parts 13 is desirably higher than the Young's modulus of the container 11. That is, it is preferred that the material of the pinching parts 13 is harder than the material of the container 11. According to this, even if the container 11 is deformed by being pressing, the pinching parts 13 are deformed less than the container 11. Since the pinching parts 13 are deformed less, a pressure can be applied to the biological tissue while firmly pinching the biological tissue with the pinching parts 13.

Hereinabove, the invention made by the present inventors has been specifically described based on the embodiments, however, the invention is not limited to the previously described embodiments, and it is a matter of course that various modifications may be made without departing from the gist of the invention. Hereinafter, modifications will be described.

First Modification

In the above-mentioned configuration, it is described that the tips of the pinching parts 13 are in an open state when a pressure is not applied, however, a configuration in which the tips of the pinching parts 13 are closed when a pressure is not applied may be adopted. In this case, the tips of the pinching parts 13 will open when a pressure is applied. Even in this case, gripping of a biological tissue, transfer, and isolation can be smoothly performed.

Second Modification

Figure 4:
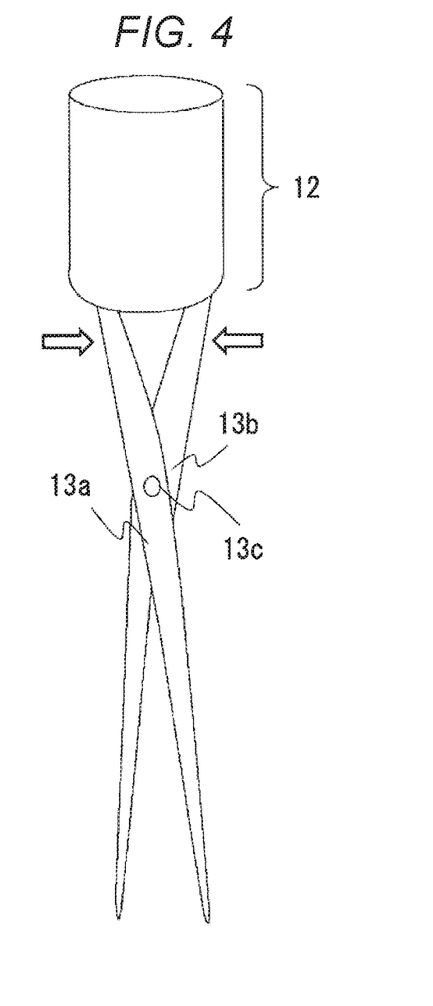
FIG. 4 is a view showing the configurations of a sealing member 12 and pinching parts 13 according to the embodiment of the present disclosure.

The shape of the pinching parts 13 described above is merely example, and may be another shape. A modification of the pinching parts 13 is shown in FIG. 4. In this modification, the pinching part 13a and the pinching part 13b are coupled with each other with a fulcrum member 13c. A medical worker performs pressing and release of pressing of the vicinity of the portion of attaching the pinching parts 13 to the sealing member 12 (for example, the portion indicated by the arrows in FIG. 4), thereby opening and closing the tips of the pinching part 13a and the pinching part 13b (bringing the tips into and out of contact with each other).

Even in the case of this configuration, a biological tissue can be pinched with the tips of the pinching part 13a and the pinching part 13b, and also cells can be isolated from the biological tissue by applying a pressure to the biological tissue when pinching the biological tissue. That is, gripping of a biological tissue, transfer, and isolation can be performed all together, and thus, the working efficiency of the medical worker can be improved.

Also in the configuration of FIG. 4, the pinching surfaces of the pinching part 13a and the pinching part 13b may be provided with ridges and grooves (FIGS. 2B to 2D).

Incidentally, the configurations of FIGS. 1 and 4 are merely examples, and another configuration may be adopted as long as the open or closed state of the pinching parts 13 can be adjusted by pressing.

Third Modification

In the above description, a description has been given by assuming that a biological tissue is pinched with the pinching surfaces 131 of the pinching parts 13 and pressed, however, isolation of cells may be performed by pressing a biological tissue against the container 11. A configuration when using this method is shown in FIGS. 5A to 5C.

Figure 5A:
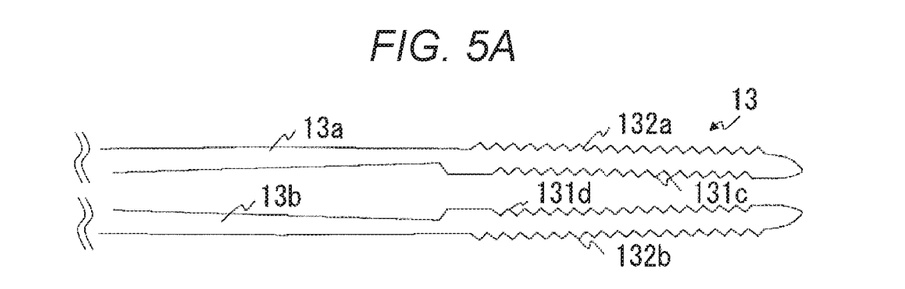
FIGS. 5A to 5C are views each showing the configurations of pinching parts 13 and a container 11 according to an embodiment of the present disclosure.

FIG. 5A is an enlarged view showing a configuration example of the pinching parts 13 to be used when isolation of cells is performed by pressing a biological tissue against the container 11. As shown in FIG. 5A, ridges and grooves are provided in a part of an opposite surface 132a facing the pinching surface 131c. In the same manner, ridges and grooves are provided in a part of an opposite surface 132b facing the pinching surface 131d. The opposite surface 132a and the opposite surface 132b are pressed against the inner wall of the container 11 in the case where the pinching parts 13 are in an open state (in the case where the pinching part 13a and the pinching part 13b act so as to be separated from each other). At this time, by sandwiching a biological tissue between the inner wall of the container 11 and the opposite surface 132a (or 132b), isolation of cells is performed. Incidentally, in FIG. 5A, a shape in which the pinching surface 131c and the pinching surface 131d have ridges and grooves is adopted, however, the shape is not necessarily limited thereto, and may be another shape (for example, any configuration of FIGS. 2A to 2D).

Incidentally, by providing ridges and grooves also in the inner wall of the container 11, isolation of cells can be more efficiently performed. FIG. 5B shows a shape having ridges and grooves on the inner wall of the container 11. As shown in FIG. 5B, ridges and grooves are provided on an inner wall surface 111a and an inner wall surface 111b of the container 11.

Figure 5B:
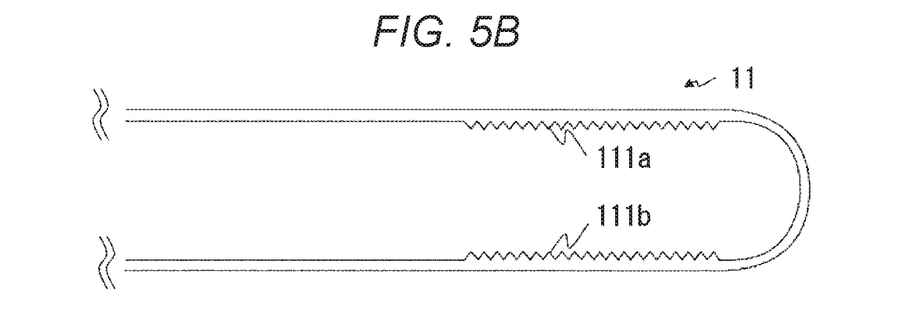
Figure 5C:
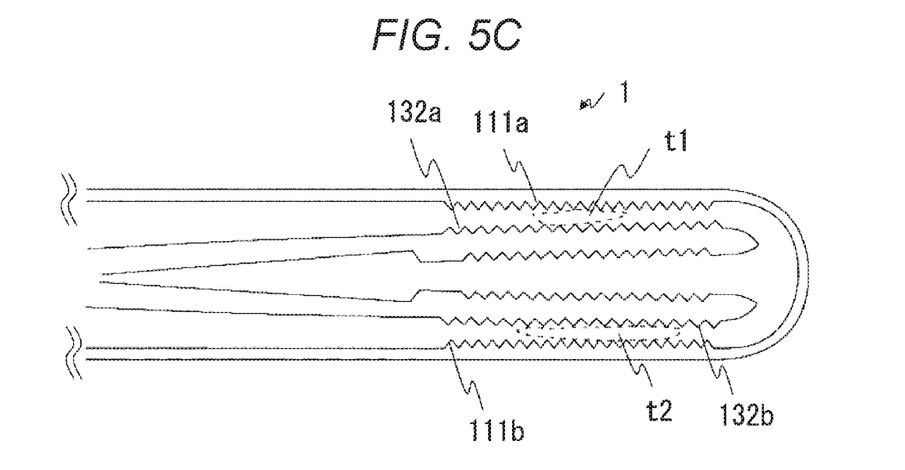

FIG. 5C is a view showing a concept of isolation of cells using the pinching parts 13 shown in FIG. 5A and the container 11 shown in FIG. 5B. As shown in FIG. 5C, a biological tissue t1 is sandwiched between the inner wall surface 11a and the opposite surface 132a. Cells are isolated from the biological tissue t1 by applying a pressure to the tissue while sandwiching the tissue. In the same manner, a biological tissue t2 is sandwiched between the inner wall surface 111b and the opposite surface 132b. Cells are isolated from the biological tissue t2 by applying a pressure to the tissue while sandwiching the tissue.

Even in the case of the configuration (FIGS. 5A and 5B), gripping of a biological tissue, transfer, and isolation can be smoothly performed.

Incidentally, even in the case of the third modification, it is preferred that the container 11 is soft such that it is deformed by being pressed by a medical worker as described above. By pressing the container 11 by medical worker, the biological tissues t1 and t2 can be pressed against the inner wall surface 111a and the inner wall surface 111b from the outside of the container 11.

Incidentally, the shape (FIG. 5B) in which ridges and grooves are provided on the inner wall surface 111a and the inner wall surface 111b of the container 11 can also be used in combination with the shape of arbitrary pinching parts 13 (for example, a shape in which ridges and grooves are not provided on the opposite surface to the pinching surface as shown in FIGS. 2A to 2D). By bringing a biological tissue into contact with the inner wall surface 111a and the inner wall surface 111b having ridges and grooves, cells are in a state of being easily isolated from the biological tissue.

Incidentally, in the example of FIG. 5B, ridges and grooves are provided on the inner wall surface 111a and the inner wall surface 111b on the side surface of the container 11, however, ridges and grooves may be provided also on the round bottom surface of the container 11. That is, any shape may be adopted as long as it is a shape with ridges and grooves on a part of the inner wall of the container 11.

Fourth Modification

Figure 6:
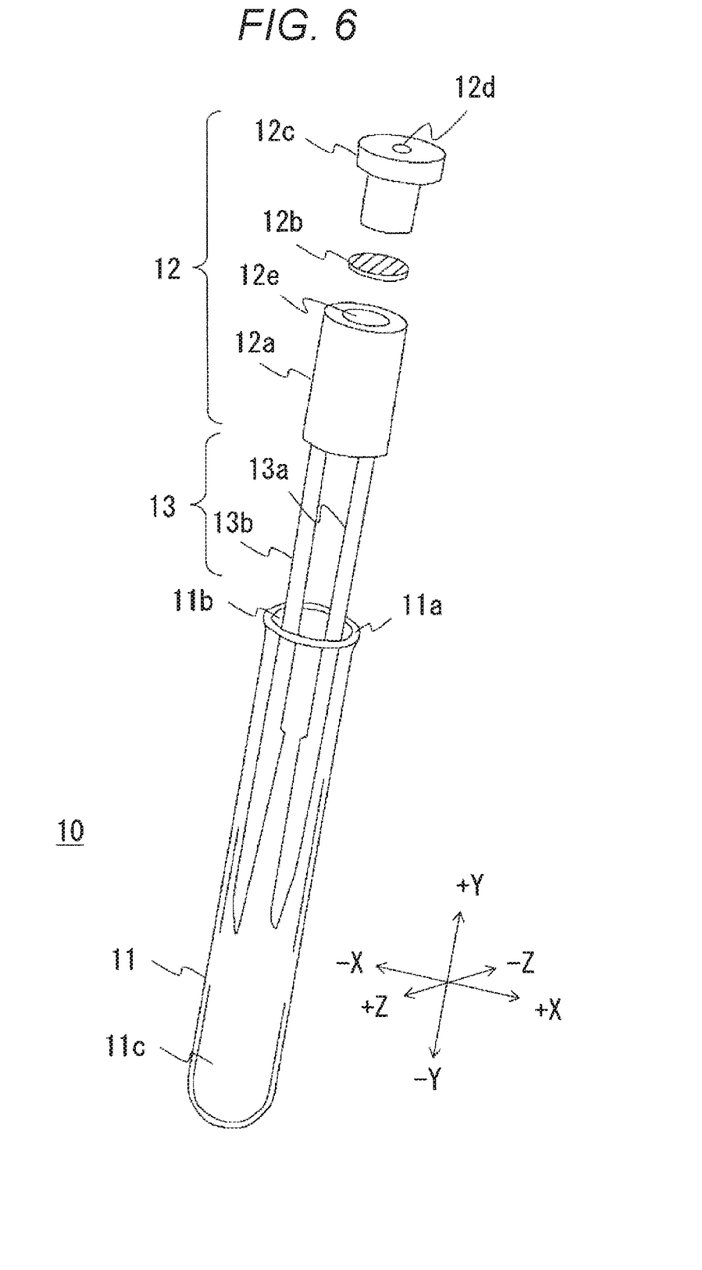
FIG. 6 is a perspective view showing the configuration of a cell isolation instrument 10 according to an embodiment of the present disclosure.

The sealing member 12 may be provided with a filter. This configuration example will be described with reference to FIGS. 6 and 7. FIG. 6 is an exploded view according to the modification of the cell isolation instrument 10. The cell isolation instrument 10 includes a container 11, a sealing member 12, and pinching parts 13 in the same manner as the configuration of FIG. 1.

In this modification, the sealing member 12 includes a large-diameter part 12a, a filter 12b, and a small-diameter part 12c. The large-diameter part 12a is a member which seals an opening 11b of the container 11. The outer diameter of the large-diameter part 12a is substantially the same as the diameter of the opening 11b of the container 11. By inserting the large-diameter part 12a into the opening 11b, the sealing member 12 is fixed to the container 11. To the insertion surface of the large-diameter part 12a into the opening 11b, the pinching parts 13 are connected. In the large-diameter part 12a, a transfer port 12e for transferring a solution (a solution containing isolated cells) placed in the container 11 to the filter 12b is provided.

The filter 12b is formed from a material free from cytotoxicity and has an aperture such that a solution containing isolated cells (cells subjected to nuclear isolation) can pass through the aperture. For example, the filter 12b is a nylon mesh with an aperture of 50 μm. The filter 12b allows the solution containing the cells to pass therethrough to the small-diameter part 12c and also prohibits unnecessary substances from flowing to the small-diameter part 12c. That is, the filter 12b filters the solution in the container 11.

The small-diameter part 12c is connected to a flow cytometer, and supplies a solution (a solution containing isolated cells) supplied from the filter 12b to the flow cytometer. Incidentally, the small-diameter part 12c may be connected to an apparatus other than the flow cytometer or a container such as a plate. In the small-diameter part 12c, a transfer port 12d for connecting the filter 12b with the upper end surface of the small-diameter part 12c is provided.

Figure 7:
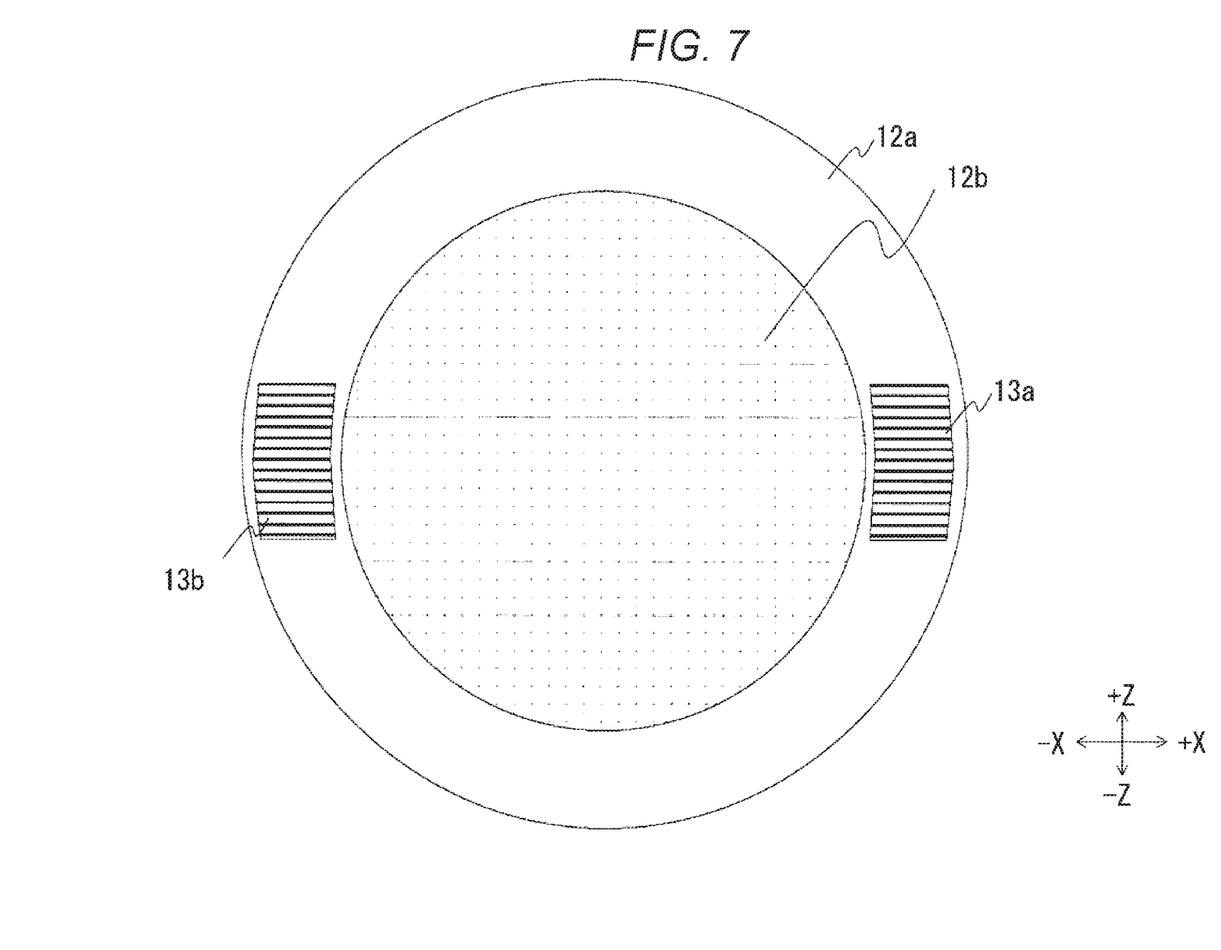
FIG. 7 is a view showing the configurations of a sealing member 12 and pinching parts 13 according to an embodiment of the present disclosure.

FIG. 7 is a conceptual view in the case where the pinching parts 13 and the sealing member 12 are referred to from the −Y direction. As shown in FIG. 7, the large-diameter part 12a has a cylindrical shape formed by hollowing out the central portion. The hollowed out portion includes a transfer port 12e through which a solution passes. In other words, the large-diameter part 12a can also be interpreted as a ring shape with a height. The filter 12b is disposed between the large-diameter part 12a and the small-diameter part 12c (not shown).

The pinching part 13a and the pinching part 13b are connected to the bottom surface of the large-diameter part 12a. For example, the pinching part 13a and the pinching part 13b may be fused to the bottom surface of the large-diameter part 12a, or may be fitted to a fitting opening of the large-diameter part 12a, or may be screwed to the large-diameter part 12a. That is, the pinching part 13a and the pinching part 13b may be connected to the large-diameter part 12a such that the tips are openable and closable (preferably, capable of coming into and out of contact with each other).

A medical worker isolates cells from a biological tissue according to the procedure shown in FIGS. 3A to 3E. In the case where it is determined that cells could be sufficiently isolated from a biological tissue, the solution (the solution containing the isolated cells) is extracted from the container 11, and the cells are analyzed by a flow cytometer. For example, the medical worker grips the cell isolation instrument 10 so that the transfer port 12d of the sealing member 12 faces the direction of gravitational force, By doing this, the solution moves to the direction of gravitational force, whereby the solution can be extracted. Incidentally, foreign substances are removed by the filter 12b. The extracted solution is in a state where the removal of RNA and the staining of the cells are completed, and therefore, the analysis by the flow cytometer can be immediately performed. Incidentally, it is also possible to extract the solution from the cell isolation instrument 10 in a state where the transfer port 12d is fitted with a nozzle of the flow cytometer.

In the above-mentioned modification (FIGS. 6 and 7), the transfer port 12d and the transfer port 12e are provided in the sealing member 12, and also the filter 12b is provided between the transfer port 12d and the container 11. The filter 12b removes impurities from the solution (the solution containing the isolated cells). According to this, an analysis can be performed with less effect of impurities

What is claimed is:

1. A cell isolation instrument, comprising:
a container including an opening;
a seal configured to seal the opening; and
a pair of pinching arms connected to the seal and the pair of pinching arms are configured to close by being pressed, wherein the pair of pinching arms includes a pinching surface for pinching a biological tissue, wherein the pair of pinching arms comprises a first pinching arm and a second pinching arm, and tips of the first pinching arm and the second pinching arm are closed when a pressure is applied to the container and the tips of the first pinching arm and the second pinching arm are open when the pressure to the container is released,
wherein at least a portion of the pinching surface includes ridges and grooves, and wherein the seal includes:
a first portion which is inserted into the opening of the container, the first portion having a cylindrical shape, the first portion provided with a first transfer port for communicating a solution containing isolated cells, the first transfer port passing through a central portion of the first portion, the first portion including an annular bottom surface radially outside of the first transfer port, the pair of pinching arms being attached to the annular bottom surface of the first portion, wherein the first transfer port is disposed between the pair of pinching arms;
a second portion provided with a second transfer port for communicating the solution with an external apparatus; and
a substantially planar mesh filter disposed between the first transfer port and the second transfer port and configured to filter the solution.

2. The cell isolation instrument according to claim 1, wherein the pair of pinching arms is in a state where tips are open when a force is not applied thereto.

3. The cell isolation instrument according to claim 1, wherein the container is configured to be deformable by being pressed.

4. The cell isolation instrument according to claim 1, wherein a Young's modulus of the container is smaller than a Young's modulus of the pair of pinching arms.

5. The cell isolation instrument according to claim 1, wherein the container includes an inner wall surface, wherein at least a portion of the inner wall surface includes ridges and grooves.

6. The cell isolation instrument according to claim 5, wherein the ridges and grooves provided on the inner wall surface of the container are used simultaneously in combination with ridges and grooves provided on a surface opposite to the pinching surface.

7. The cell isolation instrument according to claim 1, wherein the pair of pinching arms includes a surface opposite to the pinching surface, and
wherein at least a portion of the surface opposite to the pinching surface includes ridges and grooves.

8. The cell isolation instrument of claim 1, wherein the container is a glass test tube.

9. The cell isolation instrument of claim 1, wherein the container is implemented using a soft material having an elasticity of about 0.1 to 3 GPa.

10. The cell isolation instrument of claim 1, wherein the container is implemented using a material which is configured to be deformed by being pressed.

11. The cell isolation instrument of claim 10 wherein the container is implemented using a synthetic resin.

12. The cell isolation instrument of claim 11, wherein the synthetic resin is one of polypropylene, polyethylene and a combination thereof.

13. The cell isolation instrument of claim 1, wherein the pair of pinching arms includes a connecting portion that connects to the seal,
wherein an area of the pinching surface of the pair of pinching arms is larger than an area of the connecting portion of the pair of pinching arms.

14. The cell isolation instrument according to claim 1, wherein the pair of pinching arms are configured such that repeated pinching of the biological tissue and releasing of a pressure applied on the biological tissue by the pinching arms causes cells to be isolated from the biological tissue.

15. The cell isolation instrument of claim 1, wherein the second portion is to be connected to the external apparatus.

16. The cell isolation instrument of claim 1, wherein an opening area of the second transfer port at a side communicated with the external apparatus is smaller than an opening area of the first transfer port at a side of the substantially planar mesh filter.

17. The cell isolation instrument of claim 1, wherein the pair of pinching arms is attached to the annular bottom surface of the first portion by fusing with the annular bottom surface of the first portion.

18. The cell isolation instrument of claim 1, wherein the pair of pinching arms is attached to the annular bottom surface of the first portion by being fitted to a fitting opening at the annular bottom surface of the first portion.

19. The isolation instrument of claim 1, wherein the pair of pinching arms is attached to the annular bottom surface of the first portion by being screwed to the annular bottom surface of the first portion.

20. The isolation instrument of claim 1, wherein the first pinching arm and the second pinching arm are coupled to each other with a fulcrum member positioned in middle portions of the first pinching arm and the second pinching arm.

* * * * *